United States Patent [19]
Holl et al.

[11] Patent Number: 6,061,121
[45] Date of Patent: May 9, 2000

[54] DEVICE AND PROCESS FOR CHECKING SHEET ARTICLES SUCH AS BANK NOTES OR SECURITIES

[75] Inventors: Norbert Holl, Sindelfingen; Florian Holzner, Wessling; Heinz-P. Hornung, Gilching; Bernd Wunderer, Munich, all of Germany

[73] Assignee: Giesecke & Devrient GmbH, Munich, Germany

[21] Appl. No.: 08/945,796

[22] PCT Filed: May 9, 1996

[86] PCT No.: PCT/EP96/01966

§ 371 Date: Feb. 19, 1998

§ 102(e) Date: Feb. 19, 1998

[87] PCT Pub. No.: WO96/36021

PCT Pub. Date: Nov. 14, 1996

[30] Foreign Application Priority Data

May 11, 1995 [DE] Germany ............... 195 17 194

[51] Int. Cl.[7] ...................................... G06K 9/74
[52] U.S. Cl. .................................. 356/71; 250/271
[58] Field of Search ............ 356/71, 417, 445–448, 356/402–411, 237.1–237.6, 385; 355/133; 250/271, 556, 557, 559.01, 559.16–559.18, 548, 559.44; 382/7, 112, 135; 283/901–902; 209/534, 587, 576–577; 399/366, 221

[56] References Cited

U.S. PATENT DOCUMENTS

| | | |
|---|---|---|
| 4,542,829 | 9/1985 | Emery et al. . |
| 4,710,963 | 12/1987 | Chapman et al. . |
| 4,943,159 | 7/1990 | Oetliker et al. . |
| 5,026,159 | 6/1991 | Allen et al. . |
| 5,471,281 | 11/1995 | Hayashi et al. . |
| 5,724,437 | 3/1998 | Bucher . |

FOREIGN PATENT DOCUMENTS

| | | |
|---|---|---|
| 0537513A1 | 4/1993 | European Pat. Off. . |
| 4438746Al | 5/1995 | Germany . |
| WO91/03031 | 3/1991 | WIPO . |

*Primary Examiner*—K P Hantis
*Attorney, Agent, or Firm*—Bacon & Thomas

[57] ABSTRACT

An apparatus for testing sheet material includes an illumination device which illuminates the sheet material continually and in the total spectral region to be tested, and a receiving device having at least two linear parallel CCD arrays. A filter transmitting a certain spectral region is mounted on each CCD array. The individual filters are selected so that at least one transmits in the visible spectral region and one in the invisible spectral region. For detection of the light diffusely reflected or transmitted by the sheet material, the individual CCD arrays produce electric signals from the received light which are then processed in an evaluation device and compared with reference data for testing the sheet material.

30 Claims, 9 Drawing Sheets

DEVICE AND PROCESS FOR CHECKING SHEET ARTICLES SUCH AS BANK NOTES OR SECURITIES

BACKGROUND OF THE INVENTION

1. Field of Invention

This invention relates to an apparatus and method for testing sheet material such as bank notes or papers of value.

2. Description of Related Art

EP-A 0 537 513 shows such an apparatus wherein the authenticity of bank notes is tested. For this purpose the bank note is first illuminated with light-emitting diodes in the colors, red and green, and in the infrared spectral region. The light-emitting diodes are pulsed sequentially so that the bank note is only illuminated with one color or in the infrared spectral region at a time. The diodes are disposed on both sides of the bank note. The light transmitted or reflected by the bank note is detected by means of a single linear CCD array and converted into electric signals which are then further processed accordingly.

By using a linear CCD array one can achieve a relatively high local resolution on the bank note. However, a disadvantage is the high equipment expense necessary for illuminating the bank note in different colors or in the infrared spectral region. A special problem is mutually balancing the illumination levels in the different colors or in the infrared spectral region.

DE-OS 38 15 375 shows a further apparatus for testing the authenticity of sheet material. It is constructed from a plurality of like modules. Each module has its own illumination device with white light and a linear photodiode array. Further, before each module is a filter which transmits for example the colors, red, green or blue, or in the infrared spectral region.

For testing the sheet material, the light emitted by the illumination device passes through the filter of the corresponding module and illuminates the sheet material. The light diffusely reflected by the sheet material then passes through the filter of the module and is detected by the linear photodiode array. The latter converts the impinging light into corresponding signals which are then further processed.

SUMMARY OF THE INVENTION

By using like modules for the individual colors or the infrared spectral region one can ensure high ease of repair for the apparatus, on the one hand. On the other hand, however, this requires relatively high equipment expense. The use of a photodiode array permits the sheet material to be scanned virtually in its total width. However, the resolutions achieved are comparatively low.

The invention is directed to the problem of proposing an apparatus for testing sheet material which tests the sheet material with high resolution and in a plurality of spectral regions and requires comparatively low equipment expense.

This problem is solved by the features of the main claim.

The basic idea of the invention is substantially that the apparatus has an illumination device which illuminates the sheet material continually and in the total spectral region to be tested. For detecting the light diffusely reflected or transmitted by the sheet material one uses a receiving device having at least two linear parallel CCD arrays. A filter transmitting a certain spectral region is mounted on each CCD array. The individual filters are selected such that at least one transmits in the visible spectral region and one in the invisible spectral region. The individual CCD arrays produce from the received light electric signals which are then processed in an evaluation device and compared with reference data for testing the sheet material.

The advantage of the invention is that both the illumination device and the receiving device require low equipment expense. The individual CCD arrays and corresponding filters can be disposed compactly on a carrier and are relatively cost-effective to produce. The use of a plurality of CCD arrays permits a plurality of different spectral regions to be detected simultaneously with high resolution and over the total width of the sheet material.

In a preferred embodiment the receiving device has four parallel CCD arrays with filters, the filters each transmitting a spectral region in the color range, red, green, blue, and in the infrared spectral region.

During testing of the sheet material the visible printed image of the sheet material can be tested for example by means of the color ranges, red, green and blue. Simultaneously the signals detected in the infrared spectral region can be used for determining the degree of soiling of the sheet material.

The illumination device provided preferably illuminates the sheet material uniformly in a two-dimensional illumination area. This minimizes equipment expense for correcting different illumination levels on the individual picture elements of the CCD arrays.

BRIEF DESCRIPTION OF THE DRAWINGS

FIGS. 5a–c show a schematic diagram of a uniform illumination device in the transport direction.

DETAILED DESCRIPTION OF THE PREFERRED EMBODIMENTS

Figure 1:
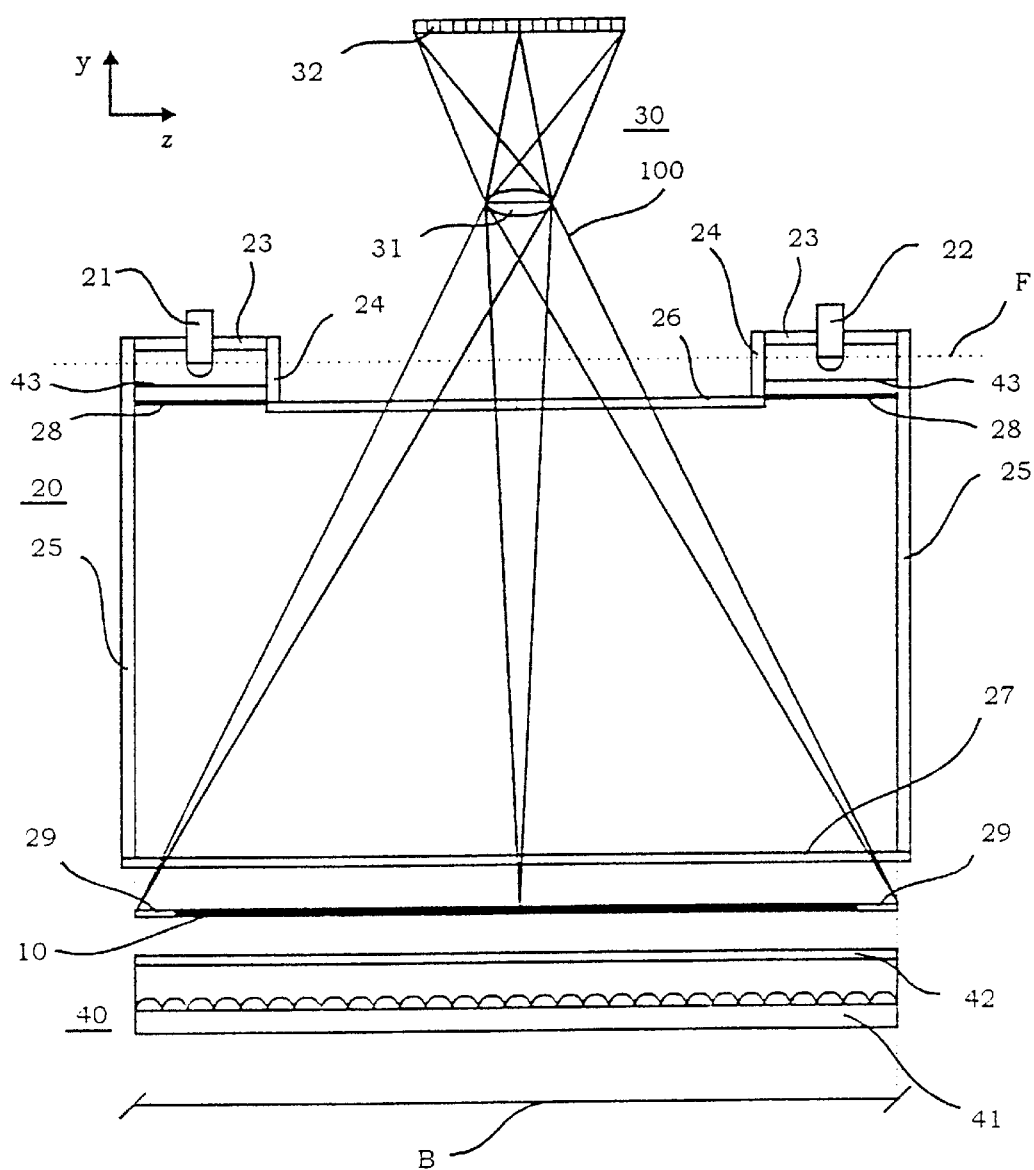
FIG. 1 shows a front view of a first embodiment of the invention.

FIG. 1 shows a front view of a first embodiment of the invention. Sheet material 10 is illuminated in an illumination area continually and in the total spectral region to be tested by means of illumination device 20. Light 100 coming from sheet material 10 is then detected by means of receiving device 30. Illumination device 20 and receiving device 30 are preferably disposed in an axis perpendicular to sheet material 10. Illumination device 20 is executed such that light 100 coming from the sheet material can pass through illumination device 20 before being detected by receiving device 30.

Illumination device 20 can optionally have back illumination device 40 which illuminates sheet material 10 from the side facing away from receiving device 30. The light emitted by back illumination device 40 is transmitted by sheet material 10 and then detected by receiving device 30.

Receiving device 30 consists substantially of optical unit 31 which images the illumination area on sheet material 10 at least partly onto photosensitive sensor 32.

Sensor 32 has at least two linear parallel CCD arrays, a filter being mounted on each CCD array. At least one filter transmits in the visible spectral region and at least one in the invisible spectral region.

Figure 4A:
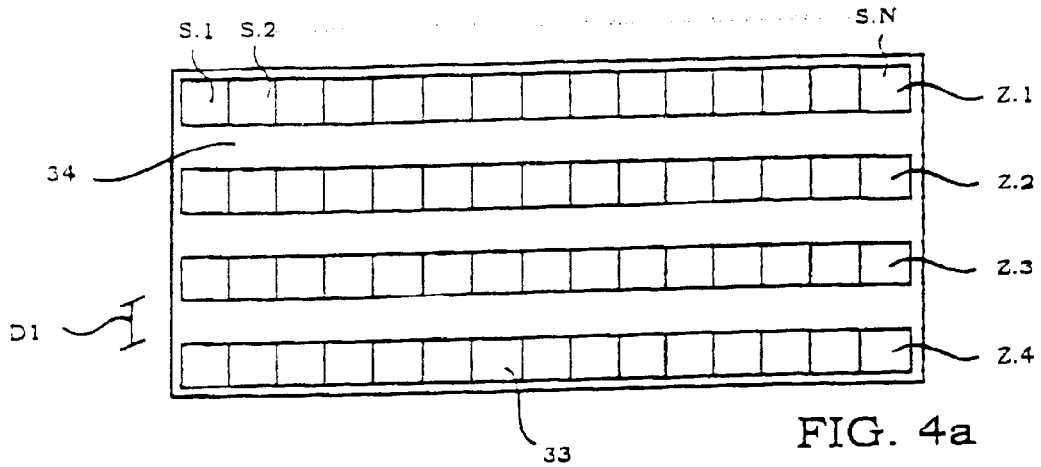
FIGS. 4a–c show a schematic diagram of a preferred embodiment of the receiving device.
Figure 4B:
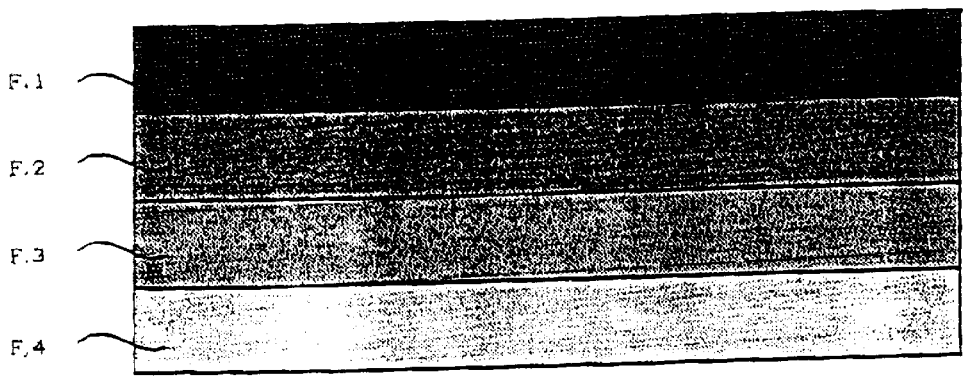
Figure 4C:
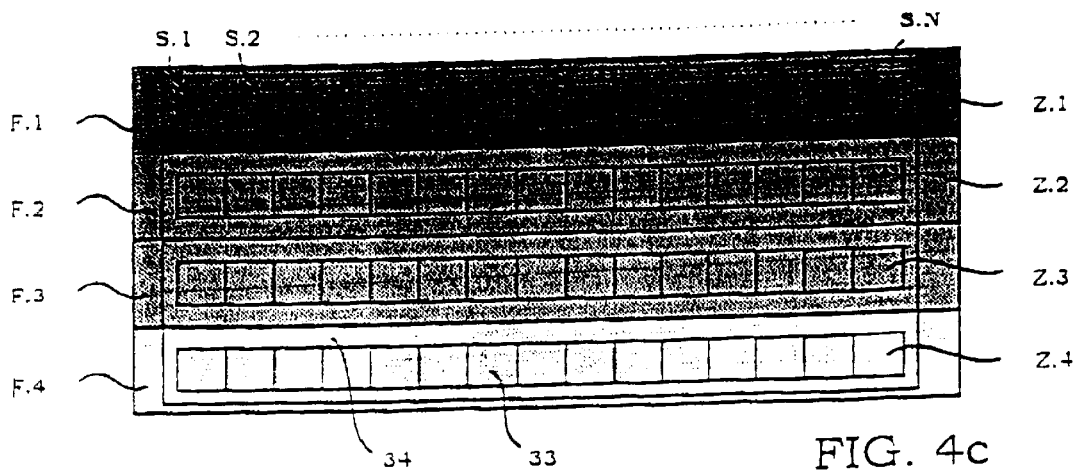

In a preferred embodiment of sensor 32, the latter has four CCD arrays Z.1–Z.4 mounted on carrier 34, as shown in FIG. 4a. Each CCD array has a plurality of picture elements 33 disposed in columns S.1–S.N. Individual CCD arrays Z.1–Z.4 are disposed parallel to each other at distance D1. FIG. 4b shows four linear filters F.1–F.4, at least one filter transmitting in the visible spectral region and at least one filter in the invisible spectral region. FIG. 4c shows a plan view of sensor 32 having carrier 34 with CCD arrays Z.1–Z.4 and linear filters F.1–F.4 mounted on the CCD arrays. Each CCD array is covered by a filter of a certain spectral region.

Sensor 32 is of compact construction, the side lengths of carrier amount 34 being a few centimeters at most. Since sensor 32 is relatively cost-effective to produce it can easily be replaced by a new sensor in case of a defect in one of CCD arrays Z.1–Z.4.

FIG. 1 further shows illumination device 20 having two light sources 21 and 22 which emit light continually in a certain spectral region. This certain spectral region is preferably the same as the spectral region to be tested. The light sources used can be for example incandescent lamps 21, 22.

Due to the radiation characteristic of light sources 21 and 22 the illumination area of sheet material 10 is illuminated unevenly both in the transport direction and perpendicular to the transport direction. This effect adversely affects light 100 diffusely reflected by sheet material 10 and thus also the illumination levels detected by sensor 32 and can hardly be compensated after detection by sensor 32.

To avoid this effect it is favorable to illuminate the illumination area of sheet material 10 virtually uniformly. For this purpose one preferably provides a reflector having cylindrical mirror segment 23 and a plurality of mirrors 24, 25 and reflecting the light emitted by light sources 21 and 22 such that the sheet material is illuminated uniformly in an illumination area with width B perpendicular to the transport direction and length L in the transport direction.

Mirror segment 23 has width B and focal line F in the direction of width B. Light sources 21 and 22 are mounted in focal line F of mirror segment 23. The form of the base line of mirror element 23 is selected so that the light emitted by light sources 21 and 22 uniformly illuminates an illumination area with width B and length L.

Figure 2:
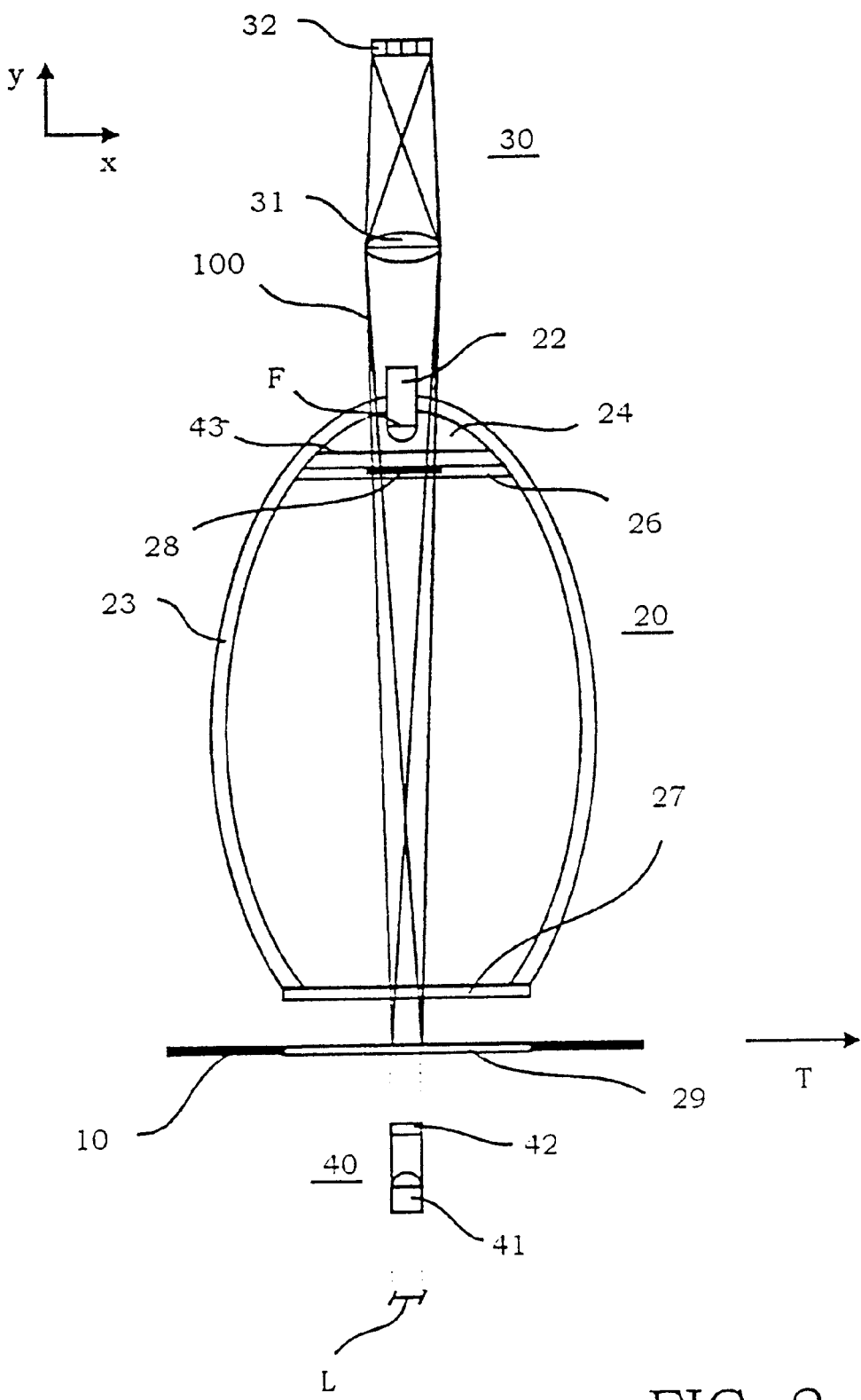
FIG. 2 shows a side view of the first embodiment of the invention.

The form of the base line of mirror segment 23 is shown in FIG. 2 and resembles an ellipse. Unlike an elliptical mirror, however, mirror element 23 has only one focal line F. The second focal line of an elliptical mirror segment is changed by the form of mirror segment 23 such that the illumination area is uniformly illuminated on the length of zone L in the plane of the sheet material.

Figure 5A:
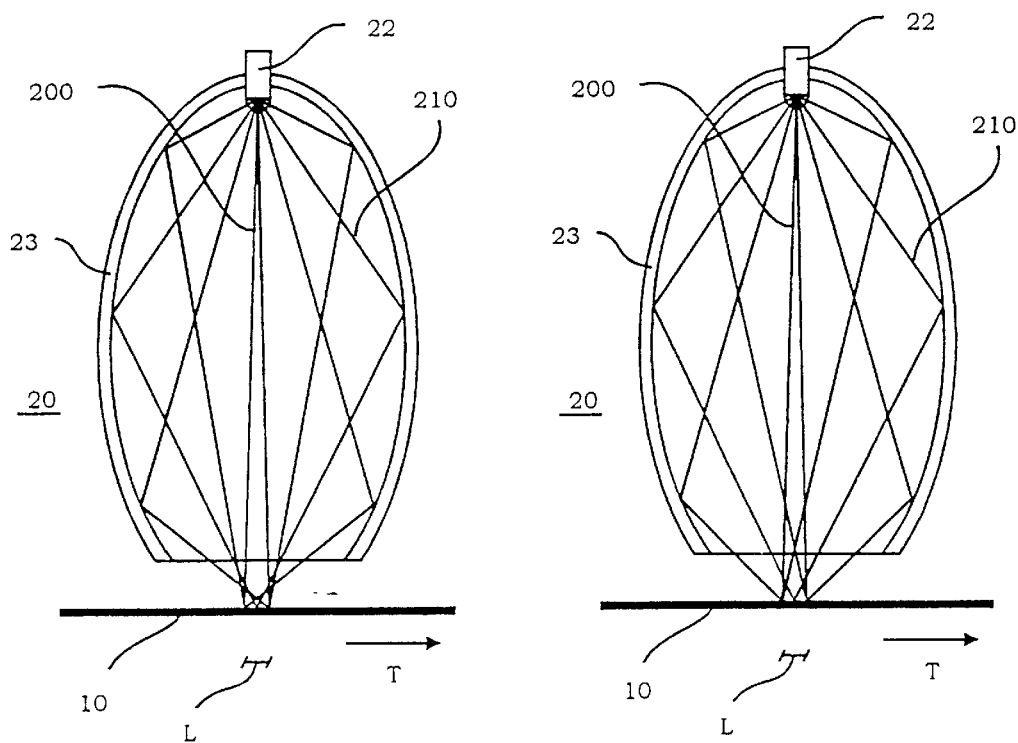
Figure 5B:
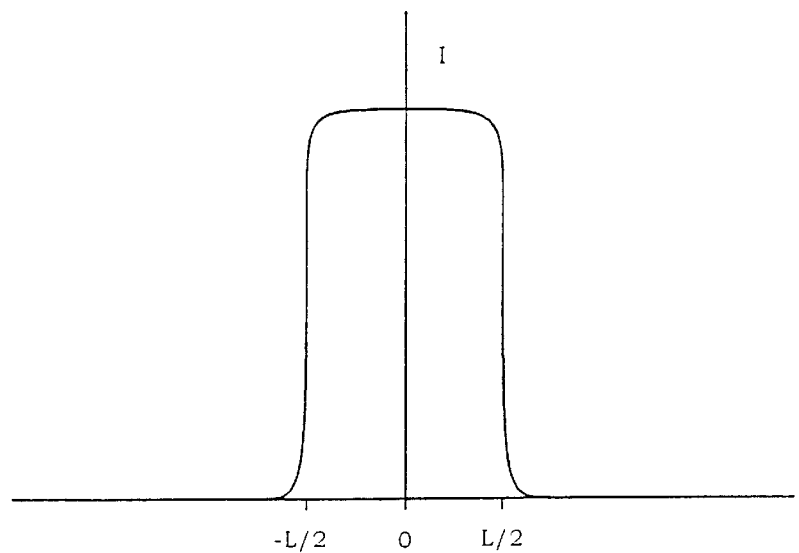

FIG. 5a shows two possible variants of the form of mirror segment 23. In the first variant the base line of mirror segment 23 is within an imaginary ellipse and in the second variant outside it. The imaginary ellipse is not shown here since the deviations are so small in the representation selected here that the viewer cannot resolve them. The light impinging on sheet material 10 is composed of direct light fraction 200 and reflected light fraction 210. The deviation from the elliptical form gives rise in both variants to an illumination level which illuminates the illumination area in length L thereof virtually uniformly, as shown in FIG. 5b.

Further, the reflector shown in FIG. 1 has two plane inner mirrors 24 within mirror segment 23 and two outer plane mirrors 25 at the ends of mirror segment 23. Mirrors 24, 25 are disposed perpendicular to focal line F of mirror segment 23, and the mirror surfaces of inner mirrors 24 and outer mirrors 25 point to one of light sources 21, 22 in each case.

Figure 6A:
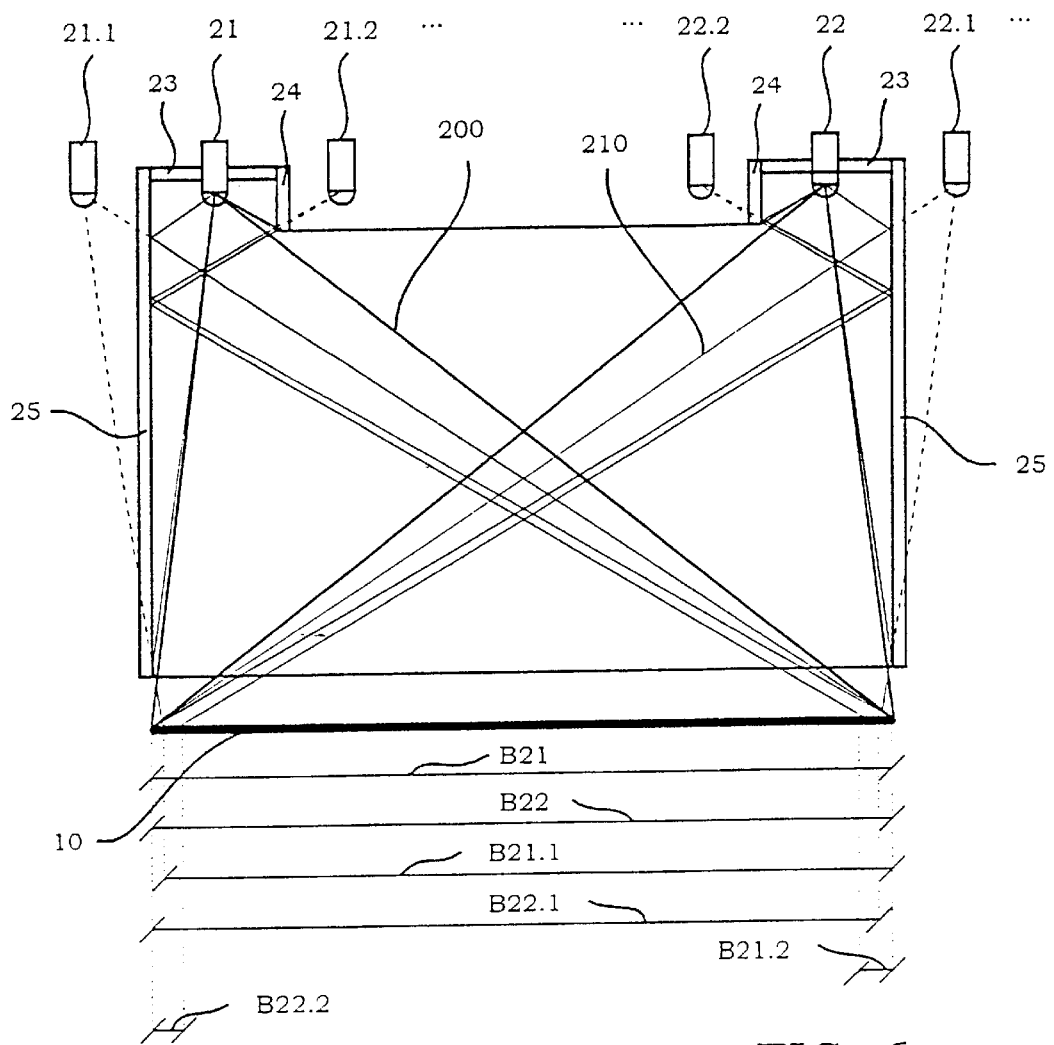
FIGS. 6a–b show a schematic diagram of the uniform illumination device perpendicular to the transport direction.
Figure 6B:
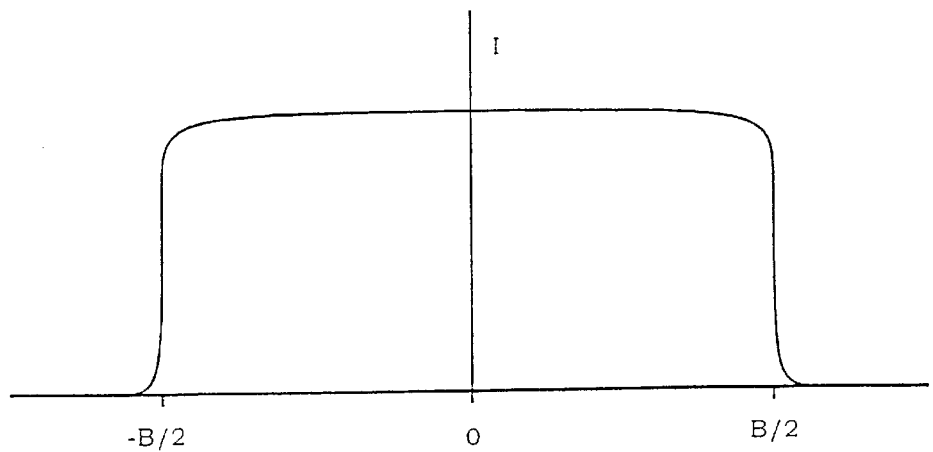

FIG. 6a shows the effect of mirrors 24 and 25 on the light emitted by light sources 21 and 22. Since each light source 21, 22 is disposed between two mirrors 24 and 25, multiple reflection of the light emitted by light source 21, 22 gives rise to quasi infinitely many virtual light sources 21.1, 21.2, etc., and 22.1, 22.2, etc. The light illuminating the illumination area in the direction of the width is therefore composed of a direct light fraction in area B21 and B22 and the light fractions of virtual light sources B21.1, B21.2, etc., and B22.1, B22.2, etc. This effect also yields a virtually uniform illumination level in the direction of the width of the illumination area, as shown in FIG. 5b.

Due to the special design of the reflector from mirror segment 23, inner mirrors 24 and outer mirrors 25, the light emitted by light sources 21 and 22 is changed such that the illumination area is illuminated uniformly both in width B and in length L. Width B is preferably selected to be at least as wide as the sheet material so that sheet material 10 can be scanned in the total width. The uniform illumination area is now imaged by optical device 31 onto sensor 32 so that the latter would also be illuminated uniformly with a uniformly reflecting background. Corrections due to uneven illumination can therefore be largely avoided.

In order to protect the reflector from soiling or moisture one can optionally close it by means of upper window 26 and lower window 27.

Figure 3:
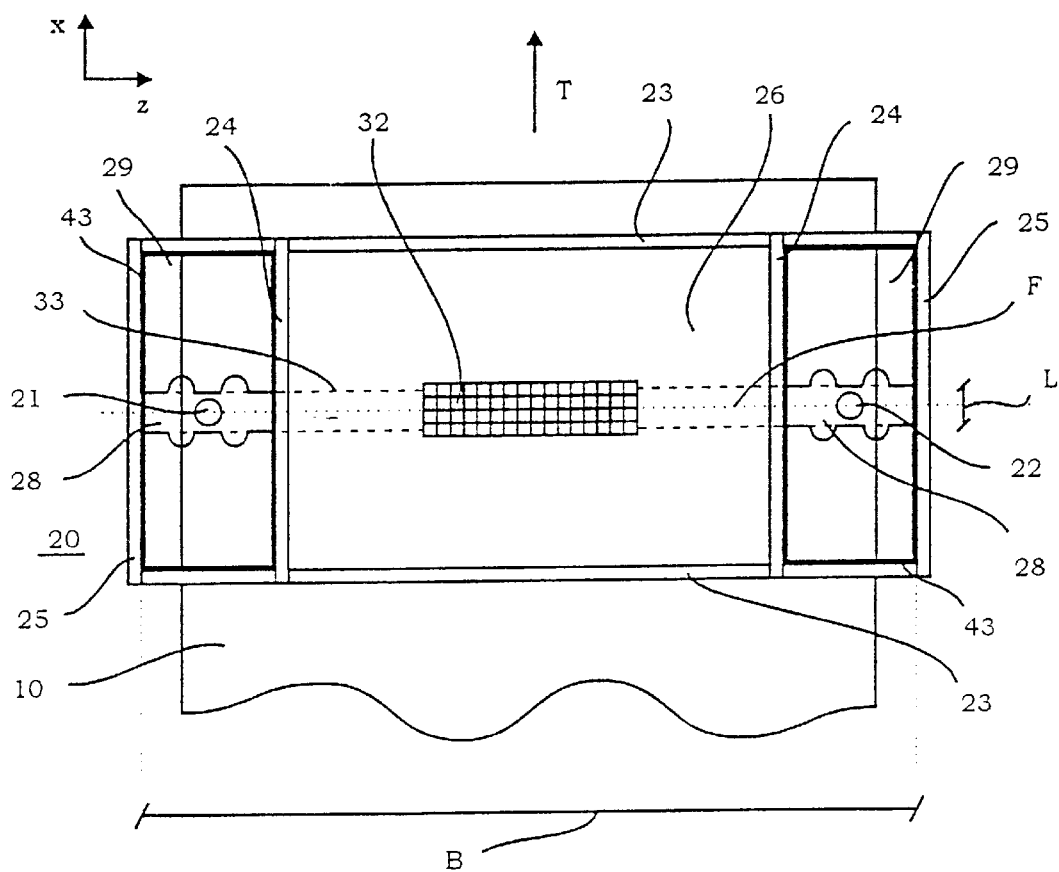
FIG. 3 shows a plan view of the first embodiment of the invention.

In order to prevent reflection of light fractions by windows 26, 27 into receiving device 30 one can bloom the corresponding surfaces of windows 26 and 27. Further, one can provide screens 28 in the reflector, selecting their form so as to deflect the stray light fractions. One possible form of screens 28 is shown in FIG. 3. However, it depends greatly on the arrangement and form of mirrors 23, 24 and 25 or windows 26 and 27 and light sources 21 and 22.

For special applications one of windows 26 or 27 or both windows can be formed as filters for a certain spectral region.

FIG. 1 further shows back illumination device 40 as a component of illumination device 20. Back illumination device 40 has LED array 41 as a light source and illuminates sheet material 10 from the side facing away from receiving unit 30. Back illumination device 40 can optionally be closed with window 42 for protection against soiling. Window 42 can also be formed as a filter, if required, so that back illumination device 40 is restricted to a certain spectral region. The spectral region is preferably selected in the infrared spectral region for example for a soiling measurement of sheet material 10.

One can optionally provide filter 43 in the reflector for preventing the light emitted by light sources 21 and 22 in the certain spectral region of back illumination device 40 from hitting sheet material 10. In this way one can combine a diffuse reflection measurement with a transmission measurement. For example one can measure the visible printed image of sheet material 10 in diffuse reflection of the visible light and simultaneously the watermark of sheet material 10 in transmission of the infrared light.

If the certain spectral region of back illumination device 40 is also produced by light sources 21 and 22 and hits sheet material 10, one obtains the effect, known from the grease spot photometer, that changes in the thickness of the sheet material, for example in the area of a watermark, cannot be detected. This effect can be exploited for measuring the soiling of the sheet material in the area of a watermark.

For testing sheet material 10, the latter is uniformly illuminated in a certain illumination area by means of illumination device 20, as described above. This illumination area is then imaged onto sensor 32 at least partly by means of optical unit 31 of receiving device 30. Light 100 impinging there is filtered by means of filters F.1–F.4 and converted by CCD arrays Z.1–Z.4 into electric signals. Each CCD array has N picture elements 33 disposed in columns S.1–S.N. Number N of the picture elements is preferably so great that the local resolution on the sheet material corresponds to a square with a side length smaller than 0.5 mm. Assuming a maximum required width B of 120 mm, number N of the picture elements per CCD array should be >=240.

For picture elements 33 to deliver a signal with a sufficient signal-to-noise ratio they must receive a certain number of light particles and transform them into photoelectrons. At a constant resolution, constant distance between sheet material 10 and CCD array 32, constant exposure time and constant f-number of the objective, the illumination level of sheet material 10 necessary for producing a certain number of photoelectrons is approximately inversely proportional to the sensitive surface of picture element 33 on the CCD array.

The illumination level of sheet material 10 can be varied only to a limited extent since it depends on the maximum illumination level of illumination device 20. This is in turn generally limited by physical effects, such as heat buildup during production of light and heat dissipation or the like. The maximum illumination level through illumination device 20 can therefore be assumed to be constant.

The size of the sensitive surface of picture element 33 can be optimized in accordance with exposure time. The exposure time depends substantially on the desired local resolution on sheet material 10 in the transport direction, here 0.5 mm, and the desired transport speed of the sheet material. At a desired transport speed of 5 m/s the resulting exposure time is 0.0005/5=0.0001 s. If the light sources used are incandescent lamps with a lamp intensity less than 20 watts, one obtains the optimal size of the sensitive surface of picture element 33 of about 70×70 $\mu$m at an illumination time of 0.0001 s. With commonly used CCD arrays this size is about 13×13 $\mu$m. The CCD arrays used here are a factor of about 25 more sensitive than commonly used CCD arrays. The size of the sensitive surface can also be optimized for other transport speeds or resolutions if required.

The electric signals of individual picture elements 33 of a CCD array are amplified in an amplifier successively in the order 1, 2, . . . N and then converted into digital signals with an A-D converter. At an exposure time of 0.0001 s and number N of picture elements 33 per CCD array of 240, the resulting processing time per item of digital data is about 0.4 $\mu$s. At a higher local resolution or greater transport speed the processing time can also be shorter.

Figure 7:
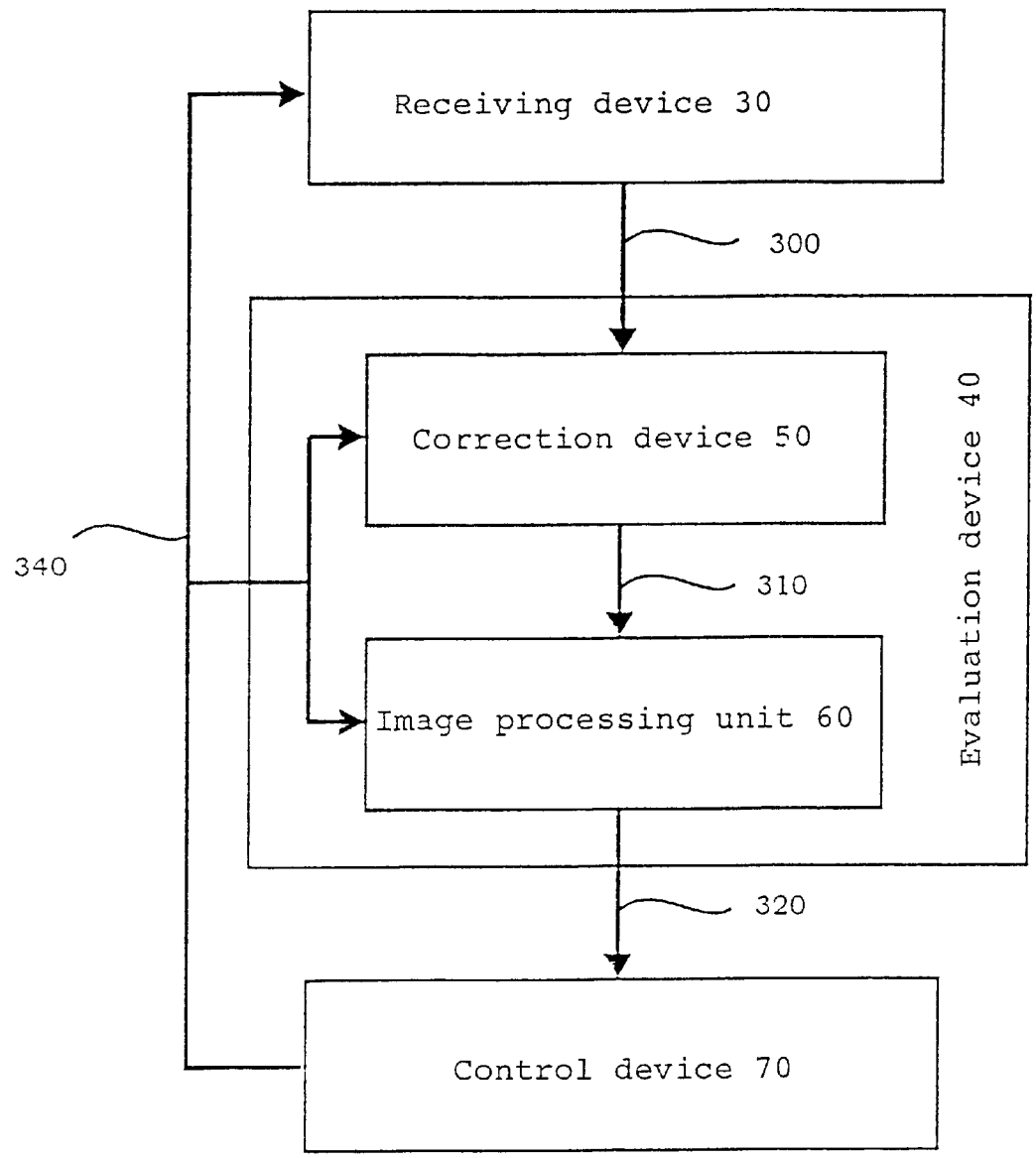
FIG. 7 shows a schematic diagram of an evaluation device.

The digital data delivered by receiving device 30 are then transferred via data line 300 to evaluation device 40 shown. This consists of two components, as shown in FIG. 7.

The first component is correction unit 50 which standardizes the digital data of individual picture elements 33 and combines the corresponding data of picture elements 33 of one column S.1–S.N of various CCD arrays Z.1–Z.4 into an item of digital data and associates it with an area on sheet material 10. The standardization is effected by means of additive and multiplicative correction variables.

Correction unit 50 contains at least one digital data processor for performing the correction calculations in the available processing time for picture element 33 of about 0.4 $\mu$s. One digital data processor is preferably provided for each CCD array Z.1–Z.4.

By additive correction of the digital values delivered by picture elements 33 one can compensate design-related differences in the dark sensitivity of the individual picture elements. The corresponding additive correction variable can be determined by a dark measurement.

Differences in measured intensity at the same illumination level can arise firstly from different sensitivity of individual picture elements 33 or from small irregularities in illumination. These differences can be compensated by multiplying the digital data by a suitable multiplier. This multiplier is determined by measurement of a white reference (ideal white surface). The white reference can be realized for example as a white background behind sheet material 10 and be measured in the gaps between two sheets. Another possibility is to insert and accordingly measure a white reference in the form of a sheet from time to time.

Further, there can be changes in illumination time which can arise e.g. from fluctuations in the control cycle of the apparatus or from slip of the sheet material in the transport system. In order to compensate such changes one again multiplies the digital data of picture elements 33 by a suitable multiplier. One determines the latter by measuring white references 29 which are disposed laterally of sheet material 10 and measured by receiving device 30 continuously during testing of sheet material 10. The digital values of picture elements 33 of sheet material 10 are standardized to the intensity measured on white reference 29 so as to exclude influences by changes in illumination time.

Individual CCD arrays Z.1–Z.4 are preferably disposed parallel at constant distance D1, distance D1 being an integral multiple of the edge length of picture element 33. Correction unit 50 is able to store a certain number of picture elements 33 in order to compensate the resulting time shift during measurement of a picture element on sheet material 10. Correction unit 30 joins the digital data of picture elements 33 disposed in one column (e.g. S.1, S.2, etc.) in various CCD arrays Z.1–Z.4 into an item of digital data such that the latter contains the information on the different spectral regions of a picture element with the desired resolution on sheet material 10. These data are then delivered via data line 310 to the second component of evaluation device 40. Data line 310 is able to transfer a data quantity of about 170 MBd. The data quantity can also be increased if required.

The second component of evaluation device 40 is image processing unit 60. It is able to assemble the digital data transferred from correction unit 50 into a two-dimensional image and store it. The stored image data can be changed for example by rotation about an axis or compression. Further, the color information of the image data can also be transformed from one color system to another (e.g. RGB to HSI). For this purpose tables can be stored in image evaluation unit 60 which contain the input value in one color system in one column and the corresponding transformed output value in the other color system in the other column. These tables permit simple and fast transformation of the color information.

For testing sheet material 10, the thus changed image data are compared with corresponding reference data in image evaluation unit 60. Depending on the quality of agreement, characteristics are determined for different tests.

Figure 8:
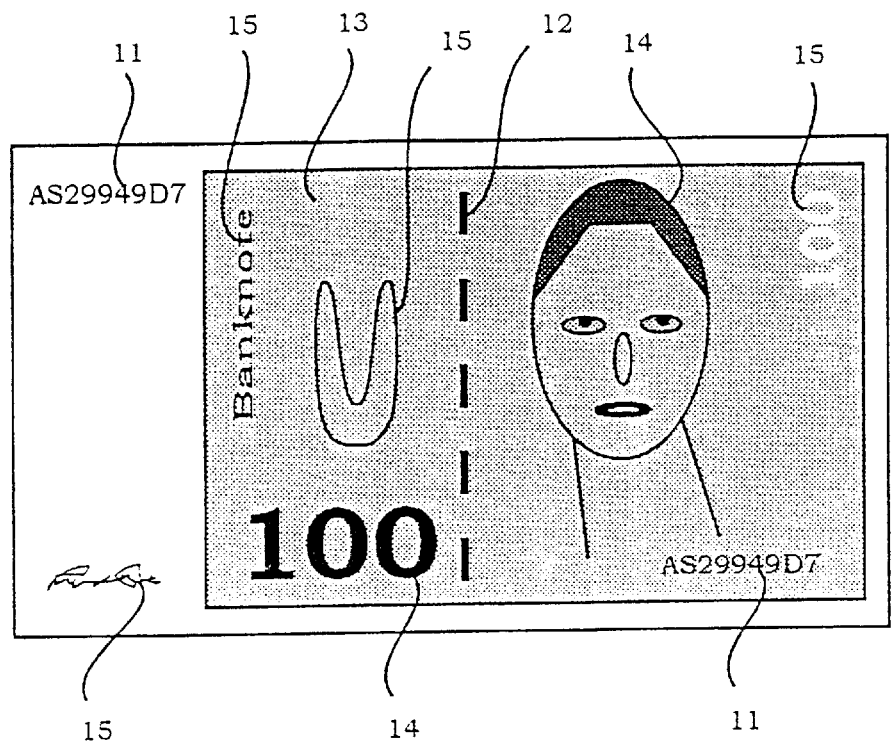
FIG. 8 shows sheet material with a printed image in the visible spectral region.
Figure 9:
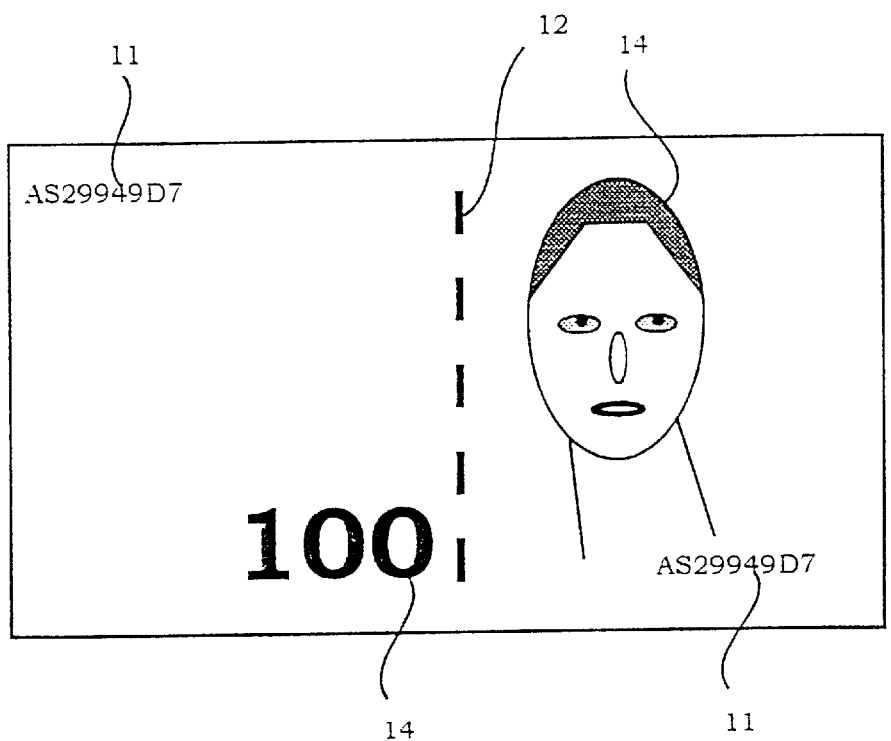
FIG. 9 shows sheet material with a printed image in the invisible spectral region.

FIG. 8 shows sheet material 10 by way of example with a schematically shown printed image of a bank note in the visible spectral region. Sheet material 10 has features which do not transmit in the infrared spectral region. These include for example serial number 11, security thread 12 and printed image 14. Further, sheet material 10 has printed images 15 which do not transmit in the visible spectral region but are transparent in the infrared spectral region. FIG. 9 shows sheet material 10 with the corresponding printed image in the infrared range.

From the visible printed image one can determine for example characteristics for the form, i.e. length or width, of sheet material 10 or the surface thereof. One can also derive characteristics for the type and transport position of the sheet material. Further, one can determine characteristics for the agreement of the printed image both in the visible and the invisible spectral regions.

Figure 10:
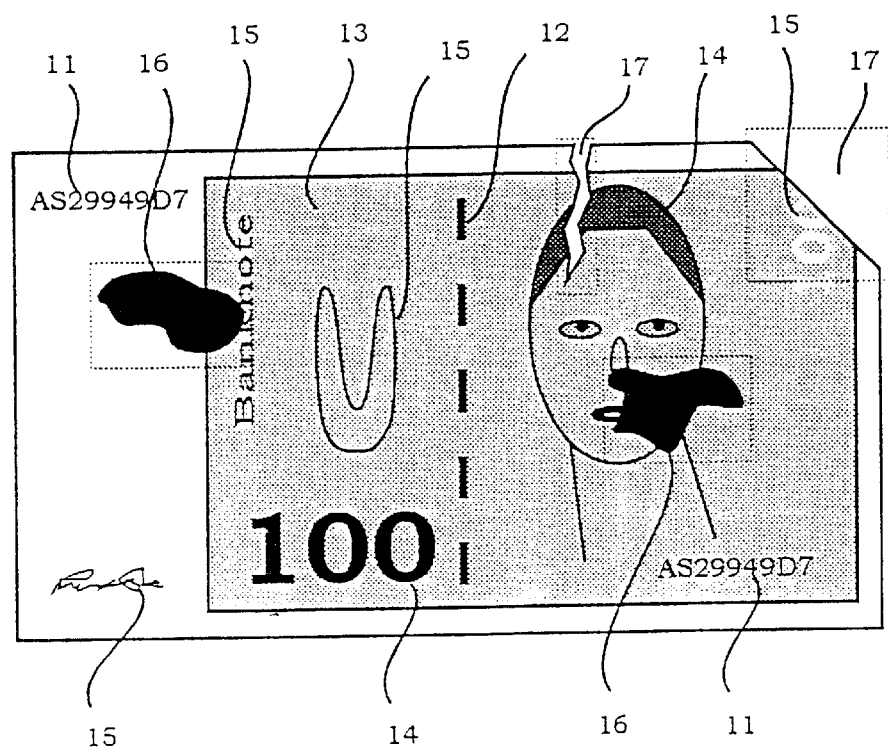
FIG. 10 shows sheet material with stains and tears in the visible spectral region.

FIG. 10 shows sheet material 10 with stains 16 and tears 17. One determines therefrom characteristics for the number of stains 17 or similar changes in the printed image by comparison with corresponding reference data on the basis of the visible printed image. In addition one can produce characteristics for the form and completeness of sheet material 10. Further, one can produce characteristics for the number of tears 17.

Figure 11:
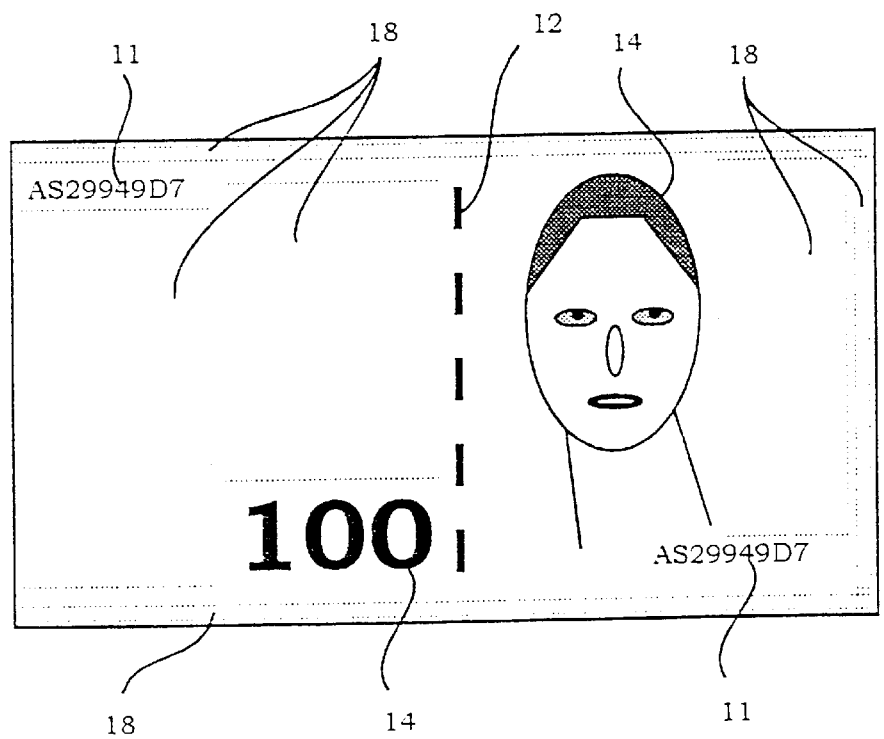
FIG. 11 shows sheet material with free areas in the invisible spectral region.

For determining characteristics of the soiling of sheet material 10 one can use free areas 18 in the infrared printed image shown in FIG. 11. Since free areas 18 are large in relation to the free areas in the visible printed image, one obtains relatively reliable characteristics for soiling.

As explained above, a further advantage of the apparatus is that a relatively great number of characteristics can be derived from the detected data. The expert can of course, if required, derive further characteristics not explicitly described here from the detected data.

The determined characteristics are preferably transferred via data line 320 to higher control unit 70. This unit decides with reference to the characteristics determined during testing, among other things, how to proceed further with sheet material 10. If required, this decision can also be made in evaluation device 40.

If the described apparatus is used for testing sheet material in a bank note processing machine for example, control device 70 can guide sheet material 10, on the basis of the characteristics of the apparatus and/or other components of the bank note processing machine, into a certain sorter pocket or into a shredder for destruction or into other components of the bank note processing machine.

We claim:

1. An apparatus for testing sheet material, said sheet material being transported during said testing at a transport speed in a transport direction, having
    an illumination device which illuminates the sheet material with light,
    a receiving device which receives light from said illumination device that is diffusely reflected by the sheet material and/or transmitted through the sheet material and that converts the light into corresponding electric signals,
    an evaluation device which processes the signals and compares them with reference data for testing the sheet material,
wherein
    the illumination device (20) illuminates the sheet material (10) uniformly in a total spectral region to be tested, and
    the receiving device (30) has at least two linear parallel CCD arrays (Z.1–Z.4),
        which are mounted on a carrier (34),
        each CCD array (Z.1–Z.4) being provided with a filter (F.1–F.4), each said filter being mounted on a respective one of said CCD-arrays and arranged to transmit a certain spectral region, and
        at least one filter mounted on a first of said CCD-arrays transmitting said light in the visible spectral region and at least one filter mounted on a second of said CCD-arrays transmitting said light in the invisible spectral region.

2. The apparatus of claim 1, wherein said at least two linear parallel CCD arrays consists of four CCD arrays arranged in parallel with each other with filters, the filters each transmitting wavelengths in the spectral region, red, green, blue (RGB), and in the infrared spectral region (IR).

3. The apparatus of claim 1, wherein the CCD arrays have picture elements with sensitive surfaces, the size of the sensitive surfaces being optimized in accordance with given parameters.

4. The apparatus of claim 1, wherein the illumination device and the receiving device are mounted in an axis perpendicular to the sheet material.

5. The apparatus of claim 1, wherein the receiving device has an optical device which images an illumination area with a certain width and length onto the CCD arrays.

6. The apparatus of claim 1, wherein the width of the illumination area is at least equal to the width of the sheet material.

7. The apparatus of claim 1, wherein the illumination area is illuminated uniformly.

8. The apparatus of claim 1, wherein the illumination device has at least one reflector and two light sources within the reflector,
    the reflector having a cylindrical mirror segment with a certain width and a focal line in the direction of the width of the mirror segment,
    the light sources being mounted in the focal line of the mirror segment,
    the form of a base line of the mirror segment being selected so that the light emitted by the light sources is uniform in the longitudinal direction of the illumination area, and
    the reflector having two plane inner mirrors within the mirror segment and two plane outer mirrors at the ends of the mirror segment, the mirrors being disposed perpendicular to the focal line of the mirror segment and the mirror surface of an inner mirror and an outer mirror pointing to one of the light sources in each case so that the illumination area is also illuminated uniformly in the direction of the width.

9. The apparatus of claim 8, wherein the reflector is closed by means of a window between the inner mirrors and a window on the side of the reflector facing the illumination area.

10. The apparatus of claim 9, wherein at least one surface of the window is bloomed.

11. The apparatus of claim 9, wherein a window is formed as a filter for a certain wavelength.

12. The apparatus of claim 9, wherein screens are provided in the reflector which prevent reflection of the light emitted by the light sources on the window facing the illumination area into the receiving device.

13. The apparatus of claim 1, further comprising a second illumination device positioned opposite the first illumination device and which illuminates a side of the sheet material facing away from the receiving device in a defined spectral region.

14. The apparatus of claim 13, wherein illumination of the sheet material in the defined spectral region of the second illumination device by other components of the illumination device is prevented by means of filters.

15. The apparatus of claim 13, wherein the defined spectral region is in the infrared spectral region.

16. The apparatus of claim 13, wherein the back illumination device has an array of light emitting diodes as a light source.

17. The apparatus of claim 13, wherein the back illumination device is closed by a window.

18. The apparatus of claim 17, wherein the window is a filter.

19. The apparatus of claim 17, wherein the window is bloomed.

20. The apparatus of claim 1, wherein the evaluation device has two components:

a correction unit which standardizes and/or combines digital data transferred by the receiving device, an image processing unit which assembles the digital data transferred by the correction unit into a two-dimensional image and then transforms and/or stores this image and compares it with reference values.

21. The apparatus of claim 1, wherein the correction unit has at least one digital signal processor for performing the calculations.

22. A method for testing sheet material, comprising the steps of:

transporting the sheet material at a transport speed in a transport direction, illuminating the sheet material continually and in a total spectral region to be tested, converting light diffusely reflected by the sheet material and/or transmitted through the sheet material in at least a visible and an invisible spectral region into digital data using at least two parallel CCD arrays mounted on a carrier and provided with corresponding filters mounted on the CCD arrays, and processing the digital data and comparing the processed digital data with reference data for testing the sheet material.

23. The method of claim 22, wherein the digital data are standardized and/or combined during said processing step.

24. The method of claim 23, wherein the digital data are standardized during said processing step to an intensity which is measured continuously by a white reference during testing in order to exclude changes due to illumination time.

25. The method of claim 22, wherein the digital data are assembled into a two-dimensional image during said processing step and this image is then transformed and/or stored.

26. The method of claim 25, wherein a color transformation of the digital data of the two-dimensional image is performed by means of stored tables during said processing step.

27. The method of claim 25, wherein a type and transport position of the sheet material is determined from two-dimensional digital data during said processing step.

28. The method of claim 25, wherein a form and completeness of the sheet material is determined from two-dimensional digital data during said processing step.

29. The method of claim 25, wherein soiling of the sheet material is determined from two-dimensional digital data during said processing step.

30. The method of claim 25, wherein two-dimensional digital data are compared with two-dimensional reference data during said processing step and stains or similar changes are recognized through the comparison.

* * * * *